United States Patent
García et al.

(10) Patent No.: US 12,144,253 B2
(45) Date of Patent: Nov. 12, 2024

(54) COMPOUND AND AN ORGANIC SEMICONDUCTING LAYER, AN ORGANIC ELECTRONIC DEVICE AND A DISPLAY OR LIGHTING DEVICE COMPRISING THE SAME

(71) Applicant: Novaled GmbH, Dresden (DE)

(72) Inventors: Elena Galán García, Dresden (DE); Johannes Scholz, Dresden (DE); Benjamin Schulze, Dresden (DE); Jens Wutke, Dresden (DE); Quan Chen, Dresden (DE); Steffen Runge, Dresden (DE)

(73) Assignee: Novaled GmbH, Dresden (DE)

( * ) Notice: Subject to any disclaimer, the term of this patent is extended or adjusted under 35 U.S.C. 154(b) by 401 days.

(21) Appl. No.: 17/430,368

(22) PCT Filed: Feb. 11, 2020

(86) PCT No.: PCT/EP2020/053437
§ 371 (c)(1),
(2) Date: Aug. 12, 2021

(87) PCT Pub. No.: WO2020/165149
PCT Pub. Date: Aug. 20, 2020

(65) Prior Publication Data
US 2022/0149290 A1 May 12, 2022

(30) Foreign Application Priority Data
Feb. 15, 2019 (EP) .................................. 19157509

(51) Int. Cl.
*C07D 471/04* (2006.01)
*C09K 11/06* (2006.01)
(Continued)

(52) U.S. Cl.
CPC ....... *H10K 85/6572* (2023.02); *C07D 471/04* (2013.01); *C09K 11/06* (2013.01);
(Continued)

(58) Field of Classification Search
CPC ............. H10K 85/6572; H10K 85/654; H10K 50/16; H10K 50/18; C07D 471/04; C09K 11/06; C09K 2211/1018
See application file for complete search history.

(56) References Cited

U.S. PATENT DOCUMENTS

| 4,219,651 A | 8/1980 | Gunther et al. |
| 2014/0088305 A1* | 3/2014 | Parham ................ H10K 85/654 438/46 |

FOREIGN PATENT DOCUMENTS

| FR | 2364214 A2 | 4/1978 |
| KR | 2013-0090726 A | 8/2013 |

OTHER PUBLICATIONS

Porokhnyak, A.O. and Turov, A.V., "Synthesis, physicochemical properties, and membrane activity of 6-(1H-benzimidazol-2-yl)benzimidazo[1,2-a]quinolines," Farmatsevtichnii Zhurnal (Kiev), (4), 61-62 (1997). (Year: 1997).*
(Continued)

*Primary Examiner* — Mark Kopec
*Assistant Examiner* — Jaison P Thomas
(74) *Attorney, Agent, or Firm* — Eversheds Sutherland (US) LLP

(57) ABSTRACT

The present invention relates to a compound having the formula (I); and an organic semiconducting layer, an organic electronic device, a display device and a lighting device comprising the same.
(Continued)

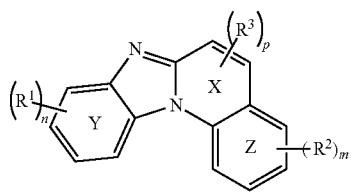

(I)

15 Claims, 2 Drawing Sheets

(51) Int. Cl.
*H10K 85/60* (2023.01)
*H10K 50/16* (2023.01)
(52) U.S. Cl.
CPC .... *H10K 85/654* (2023.02); *C09K 2211/1018* (2013.01); *H10K 50/16* (2023.02)

(56) References Cited

OTHER PUBLICATIONS

Sorokina, I.V., Porokhnyak, A.O. and Turov, A.V., "Synthesis, physicochemical properties, and membrane activity of 6-(1H-benzimidazol-2-yl)benzimidazo[1,2-a]quinolines," Farmatsevtichnii Zhurnal (Kiev), (4), 61-62 (1997). (Year: 1997).*

PCT International Search Report and Written Opinion for PCT Application No. PCT/EP2020/053437 mailed Mar. 24, 2020 (10 pages).
Dong et al., "Rhodium(III)-Catalyzed Vinylic sp2 C—H Bond Funcationalization Efficient Synthesis of Pyridol[1,2-α]-Benzimidazoles and Imidazol[1,2-α]Pyridines," Organic & Biomolecular Chemistry, 2013, 11(36):6142-6149.
Huang et al., "Synthesis of Aza-Fused Polycyclic Quinolines via Double C—H Bond Activation," Chemistry—A European Journal, 2012, 18(29):8896-8900.
Lv et al., "Synthesis of 2-Alkylaminoquinolines and 1,8-Naphthyridines by Successive Ruthenium-Catalyzed Dehydrogenative Annulation and N-Alkylation Processes," Advanced Synthesis & Catalysis, 2017, 359(7):1202-1207.
Nagesh et al., "Multicomponent Cascade Reaction: Dual Role of Copper in the Synthesis of 1,2,3-Triazole Tethered Benzimidao[1,2-α]Quinoline and Their Photophysical Studies," RSC Advances, 2016, 6(19):15884-15894.
Notification of First Office Action issued in China application No. 202080014244.9 issued Jul. 21, 2023, 24 pages.
Communication pursuant to Article 94(3) EPC issued in European application No. 19157509.1, dated Jan. 31, 2022, 5 pp.
M. Hranjec et al., Synthesis, crystal structure and spectroscopic study of novel benzimidazoles and benzimidazo [1,2-a]quinolines as potential chemosensors for different cations, Dyes and Pigments, vol. 95, No. 3, Dec. 1, 2012, pp. 644-656.
S. Manna et al., Metal-Free Annulation of Arenes with 2-Aminopyridine Derivatives: The Methyl Group as a Traceless Non-Chelating Directing Group, Angewandte Chemie International Edition, vol. 53, No. 31, Jun. 18, 2014, pp. 8163-8166.

* cited by examiner

COMPOUND AND AN ORGANIC SEMICONDUCTING LAYER, AN ORGANIC ELECTRONIC DEVICE AND A DISPLAY OR LIGHTING DEVICE COMPRISING THE SAME

CROSS REFERENCE TO RELATED APPLICATIONS

This application is a U.S. national phase application of PCT/EP2020/053437, filed Feb. 11, 2020, which claims priority to European Application No. 19157509.1, filed Feb. 15, 2019. The contents of these applications are incorporated herein by reference.

The present invention relates to a compound as well as to an organic semiconducting layer comprising the same. The invention further relates to an organic electronic device comprising the organic semiconducting layer, respectively the compound. Furthermore, the invention is related to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

Heterocyclic derivatives having nitrogen and organic electronic devices using the same are known, for example, from KR 20130090726 A.

However, there is still a need to improve the electronic properties of respective compounds for use in organic electronic devices, in particular for improving the performance thereof, and to provide respective organic electronic devices having improved performance. It is a particular aim of the present invention to improve the performance of top emission OLEDs, in particular with respect to operating voltage and efficiency thereof.

It is, therefore, an object of the present invention to provide novel organic electronic devices and compounds for use therein overcoming drawbacks of the prior art, in particular to provide novel compounds having improved properties and being suitable to improve the operating voltage and efficiency of organic electronic devices comprising the same, in particular when being used in electron transport layers thereof.

This object is achieved by a compound having the formula (I)

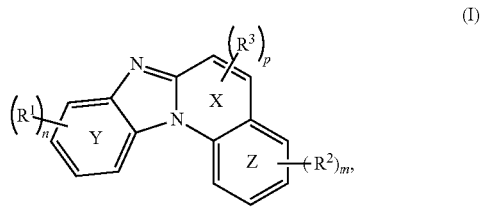

wherein
n and m are independently selected integers from 0 to 2, wherein in case that n=2 the $R^1$ can be the same or different from each other, and in case that m=2 the $R^2$ can be the same or different from each other;

p is 1 or 2, wherein in case that p=2 the $R^3$ can be the same or different from each other;

$R^1$ and $R^2$ are independently selected from the group consisting of H, substituted or unsubstituted $C_6$ to $C_{48}$ aryl and substituted or unsubstituted $C_2$ to $C_{42}$ heteroaryl, wherein the one or more substituent(s), if present, are selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, $P(=O)R_2$, wherein each R is independently selected from the group consisting of $C_1$ to $C_{20}$ linear OW, $C_1$ to $C_2$© alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{20}$ cyclic thioalkyl, $C_6$ to $C_{20}$ aryl and $C_2$ to $C_{20}$ heteroaryl and multiple R may be the same or different;

each $R^1$ and $R^2$ may be linked to the respective ring Y or Z by a first spacer unit which is independently selected from substituted or unsubstituted $C_6$ to $C_{18}$ arylene or substituted or unsubstituted $C_2$ to $C_{20}$ heteroarylene, wherein the one or more substituent(s), if present, are independently selected from the group consisting of deuterium, CN, P(=O)R'R", $C_6$ to $C_{14}$ aryl or $C_2$ to $C_{20}$ heteroaryl, wherein R' and R" may be the same or different and are independently selected from $C_1$ to $C_{10}$ alkyl or $C_6$ to $C_{12}$ aryl;

In case both of R1 and R2 are linked to the respective ring Y or Z by a first spacer unit the spacer unit for R1 may be the same as or different from the spacer unit for R2.

In case m or n>1 then the multiple first spacer units may be the same or different and independently selected.

$R^3$ is independently selected from substituted or unsubstituted $C_6$ to $C_{60}$ aryl or substituted or unsubstituted $C_2$ to $C_{60}$ heteroaryl, wherein the one or more substituent(s), if present, are independently selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, $P(=O)R_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

each $R^3$ may be linked to the ring X by a second spacer unit independently selected from substituted or unsubstituted $C_6$ to $C_{18}$ aryl or substituted or unsubstituted $C_2$ to $C_{20}$ heteroaryl, wherein the one or more substituent(s), if present, are independently selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, $P(=O)R_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

In case p=2 then the two second spacer units may be the same or different and independently selected. positions of the rings X, Y and Z which are not directly linked to either $R^1$, $R^2$, $R^3$, the first spacer unit, the second spacer unit or hydrogen may be bound to a substituent selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, $P(=O)R_2$, wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

provided that if p=1, n=0 and m=0 then it is excluded that $R^3$ is 1H-benzo[d]imidazolyl connected to the ring X without the second spacer unit.

It was surprisingly found by the inventors that the inventive compounds are suitable to improve the performance of an organic electronic device comprising the same, in particular of top emission OLEDs comprising the same in an electron transport layer thereof. In particular, it was observed that the performance of such devices can be improved with respect to operating voltage and efficiency when using the inventive compounds.

It should be understood that in the formula (I) above "X", "Y" and "Z" have no chemical meaning, i.e. are not generic expressions directed to a specific chemical moiety. Rather, the letters "X", "Y" and "Z" are merely used for denoting the very left ring, the ring adjacent to the nitrogen-containing ring and the very right ring of the benzo[4,5]imidazo[1,2-A]quinolinylene moiety comprised in formula (I) to explain the binding position between the respective rings and the groups $R^1$, $R^2$ and $R^3$.

In accordance with formula (I), the group $R^1$ may be connected to the benzo[4,5]imidazo[1,2-A]quinolinylene moiety in one of the positions labelled with the asterisk symbol "*" in the following formula

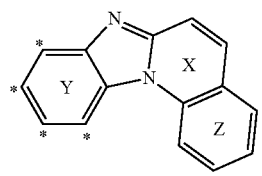

Likewise, the group $R^2$ may be connected to the benzo[4,5]imidazo[1,2-A]quinolinylene moiety in any position labelled with the asterisk symbol "*" in the following formula

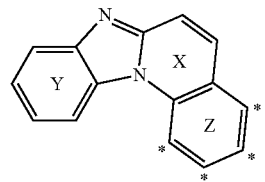

Finally, the group $R^3$ may be connected benzo[4,5]imidazo[1,2-A]quinolinylene moiety in any position labelled asterisk symbol "*" in following formula

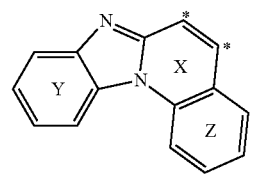

According to claim 1, it may be provided that one or more of $R^1$, $R^2$ and $R^3$ is connected to the respective ring X, Y and Z by a first spacer unit, respectively a second spacer unit. According to claim 1, it may be provided that none of the groups is connected via the spacer unit. Likewise, it may be provided that only one of the spacer units is present. Likewise, it may be provided that two or more first spacer units and two or more second spacer units are present.

The connection via the first spacer unit or the second spacer unit is achieved in that a first bond is formed between the respective spacer unit and the benzo[4,5]imidazo[1,2-A]quinolinylene moiety at one of the above positions labelled with the "*". A further bond is formed between the respective spacer unit and the respective group $R^1/R^2/R^3$. That is, the first spacer unit and the second spacer unit are divalent groups forming one bond to the respective group $R^1/R^2/R^3$ and another bond to the benzo[4,5]imidazo[1,2-A]quinolinylene moiety.

In case that m and/or n and/or p is 2, the respective spacer unit may carry one or two of the respective $R^1/R^2/R^3$.

It has been found by the inventors that certain embodiments described below are advantageous to further improve the performance of organic electronic devices comprising such compounds with respect to voltage and efficiency thereof. Best results were achieved when combining two or more of these embodiments.

With respect to the compound of formula (I), the total number of aromatic rings in the Formula (I) may be from 5 to 15, alternatively from 6 to 12.

It may be provided that p is 1 and $R^3$ is attached to the position indicated by the asterisk symbol "*" in the following Formula (Ia)

(Ia)

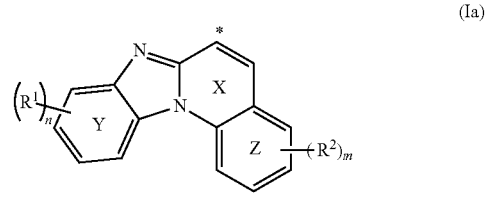

One of R³ may be unsubstituted phenyl and at least one of R¹, R² or a second R³ may be independently selected from the group consisting of substituted $C_{10}$ to $C_{40}$ aryl, substituted or unsubstituted $C_{10}$ to $C_{40}$ condensed aryl and substituted or unsubstituted $C_2$ to $C_{42}$ heteroaryl.

The first spacer unit may be selected from the group consisting of substituted or unsubstituted $C_6$ to $C_{18}$ arylene or substituted or unsubstituted N-containing $C_3$ to $C_5$ heteroarylene.

The first spacer unit may be selected from the group consisting of phenylene, naphthylene, anthracenylene, pyridinylene, diazinylene, and triazinylene, wherein the respective groups may be substituted or unsubstituted.

The groups R¹ and R² may independently be selected from substituted or unsubstituted $C_6$ to $C_{18}$ aryl, substituted or unsubstituted N-containing $C_3$ to $C_5$ heteroaryl or substituted or unsubstituted O-containing $C_4$ to $C_{12}$ heteroaryl.

R¹ and R² may independently be selected from the group consisting of phenyl, naphthyl, pyridinyl, diazinyl, triazinyl, dibenzofuranyl and triphenylenyl.

In the compound of Formula (I), n may be 0 and/or m may be 0.

The second spacer unit may independently be selected from the group consisting of substituted or unsubstituted $C_6$ to $C_{14}$ arylene and substituted or unsubstituted N-containing $C_3$ to $C_{12}$ heteroarylene.

The second spacer unit may independently be selected from the group consisting of phenylene, naphthylene, anthracenylene, biphenylene, pyridinylene, diazinylene, triazinylene, phenanthrolinylene, and quinolinylene.

R³ may independently be selected from the group consisting of substituted or unsubstituted $C_6$ to $C_{18}$ aryl, substituted or unsubstituted O-containing $C_6$ to $C_{12}$ heteroaryl and substituted or unsubstituted N-containing $C_3$ to $C_{15}$ heteroaryl.

R³ may independently be selected from the group consisting of phenyl, naphthyl, anthracenyl, pyridinyl, diazinyl, triazinyl, 9,9'-dimethylfluorenyl, triphenylenyl, 1-naphthylphenyl, carbazolyl, phenanthrolinyl, dibenzofuranyl, quinoxalinyl, quinolinyl, benzo[4,5]imidazo[1,2-A]quinolinyl and benzoacridinyl, wherein the respective groups may be substituted or unsubstituted.

The one or more substituent(s), if present in one or more of R¹, R², R³, the first spacer unit and the second spacer unit, may be independently selected from $C_6$ to $C_{14}$ aryl, N-containing $C_5$ to $C_{12}$ heteroaryl, O-containing $C_5$ to $C_{12}$ heteroaryl, CN, CN-substituted phenyl, P(=O)(CH₃)₂-substituted phenyl, P(=O)R₂ with R₂ being $C_1$ to $C_6$ alkyl or $C_6$ aryl.

The one or more substituent(s), if present in one or more of the groups R¹, R², R³, the first spacer unit and the second spacer unit, may be independently selected from the group consisting of phenyl, biphenyl, naphthyl, pyridinyl, carbazolyl, 9,9'-dimethylfluorenyl, dibenzofuranyl, triphenylenyl, CN-substituted phenyl, CN, P(=O)(CH₃)₂-substituted phenyl, P(=O)(CH₃)₂ and P(=O)Ph₂.

The compound of formula (I) may be represented by one of the following formulas 1 to 54.

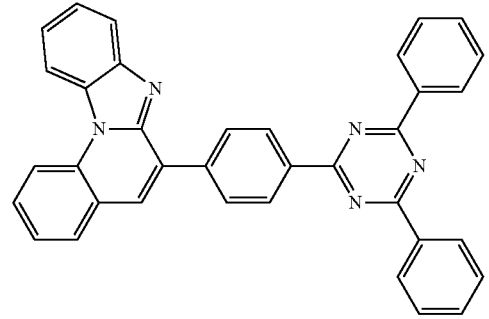

1

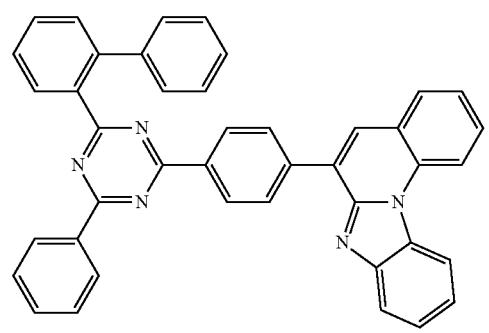

2

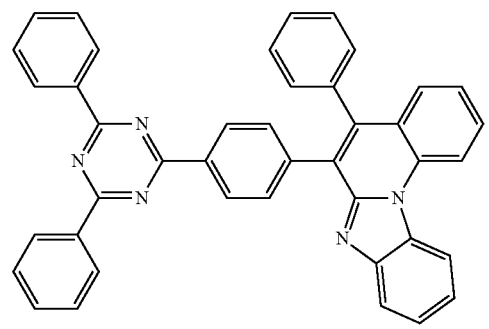

3

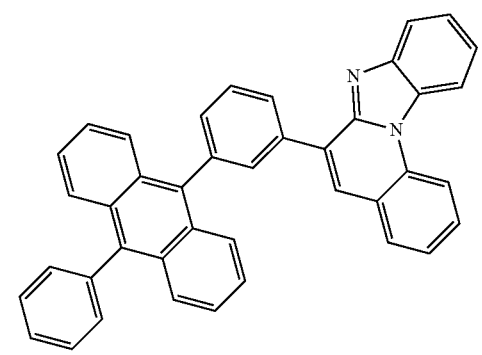

4

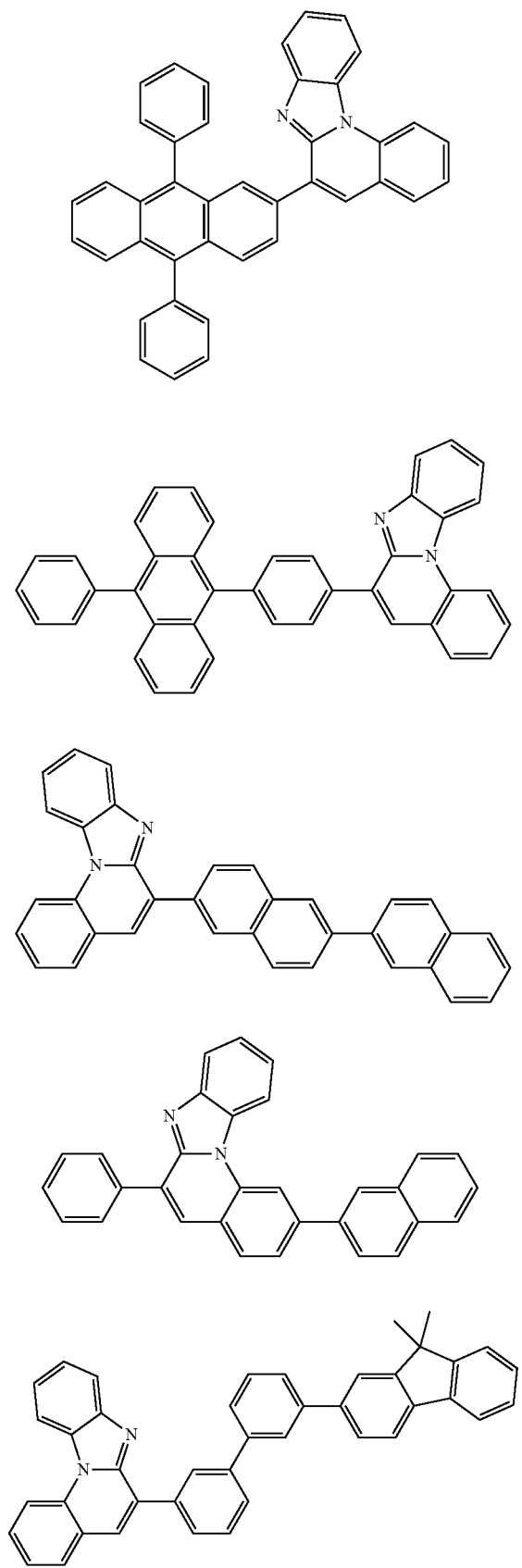
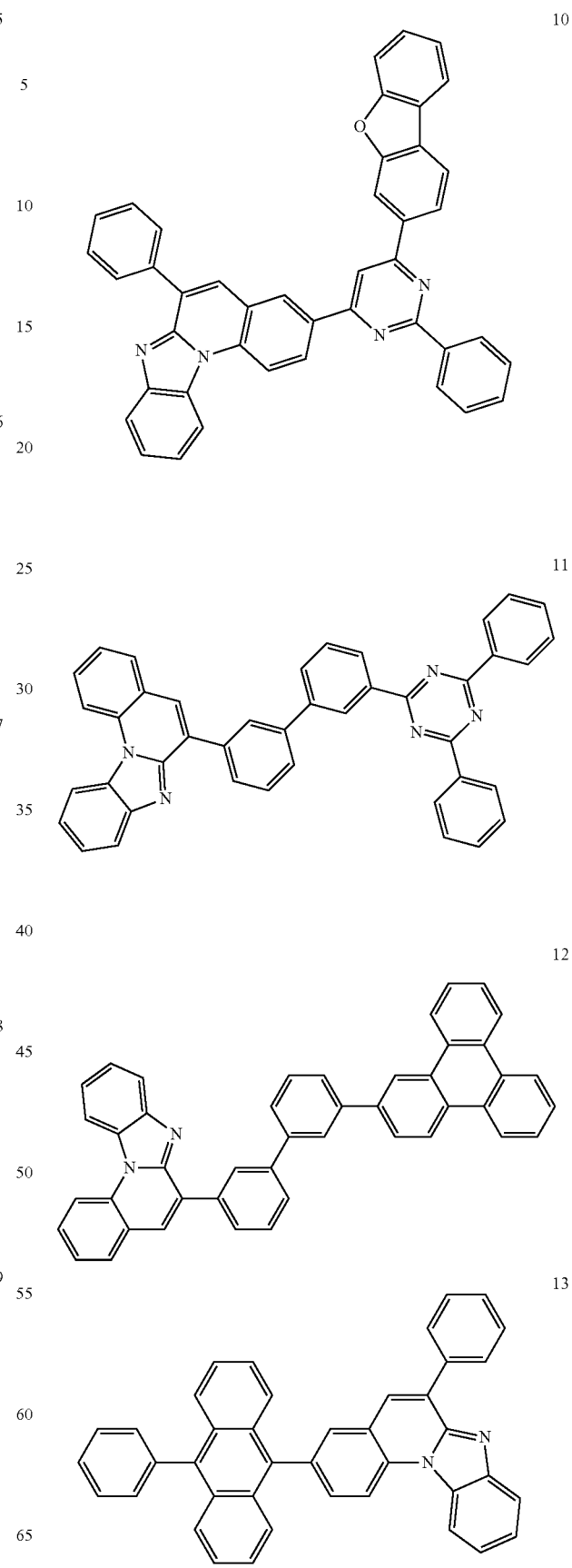

14
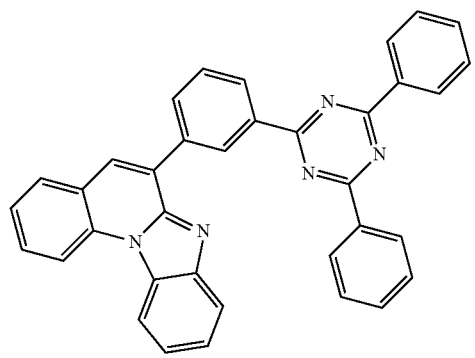
15
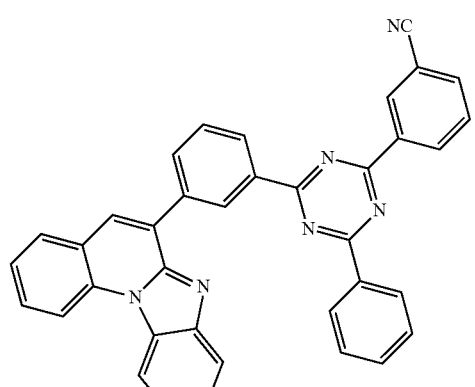
16
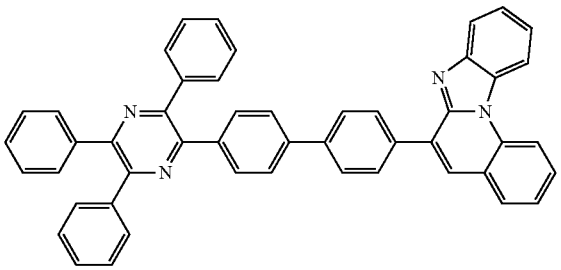
17
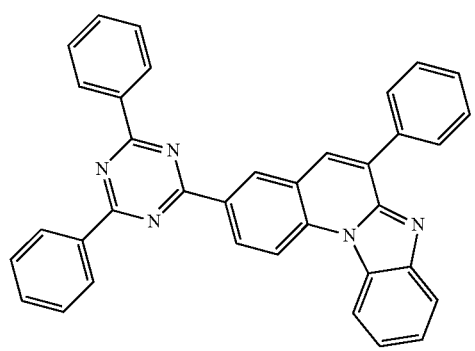
18
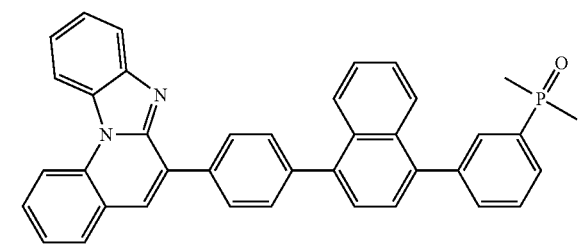
19
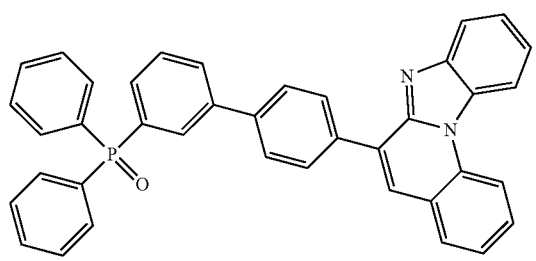
20
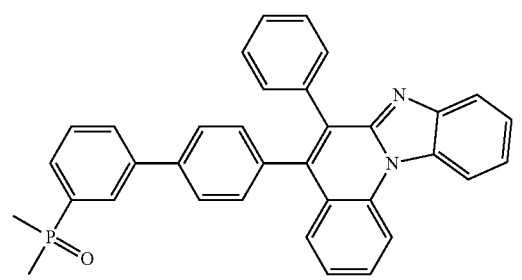
21
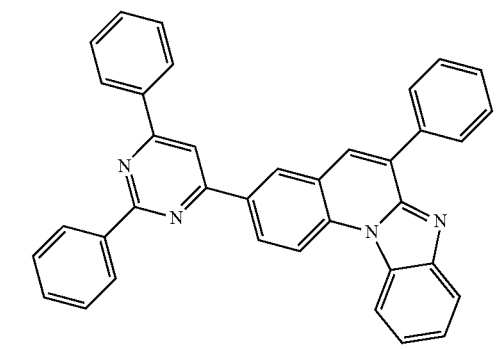
22
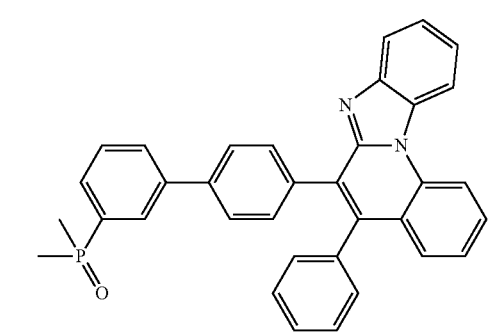

23
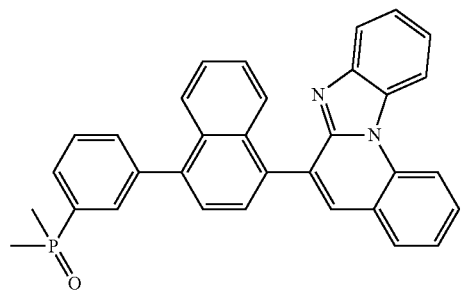
24
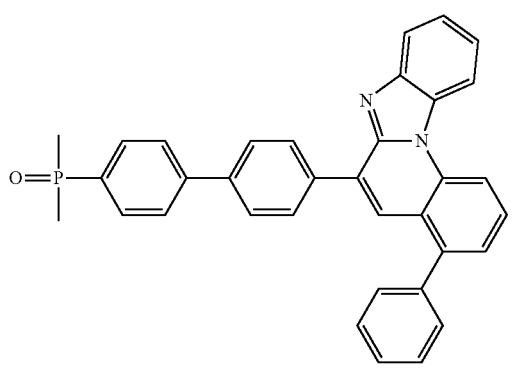
25
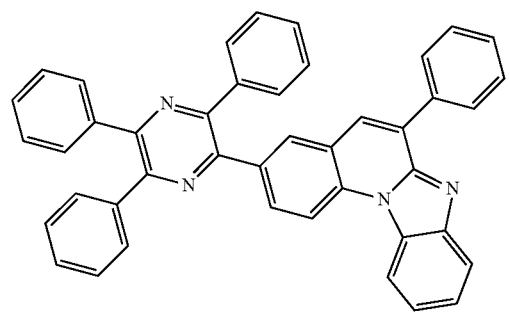
26
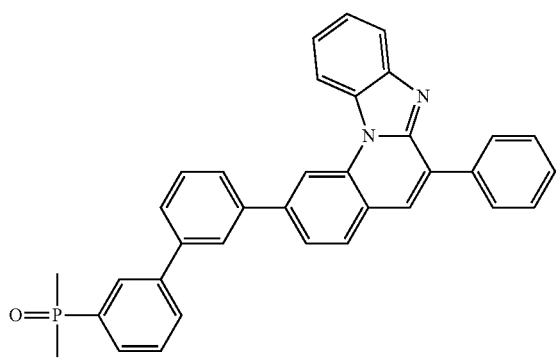
27
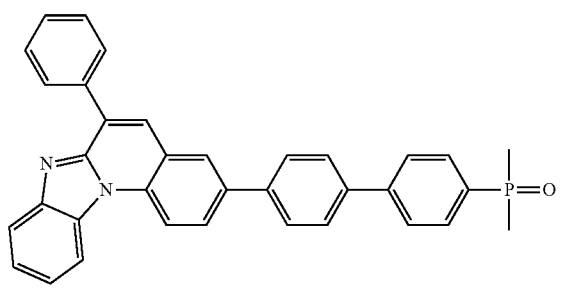
28
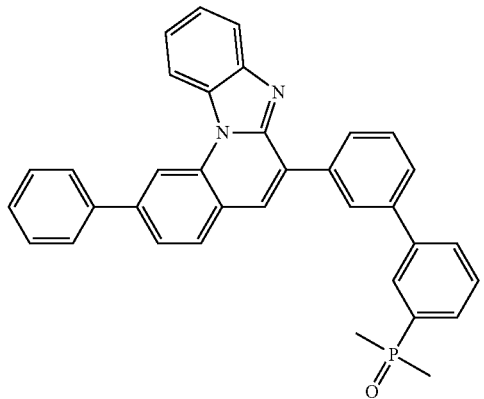
29
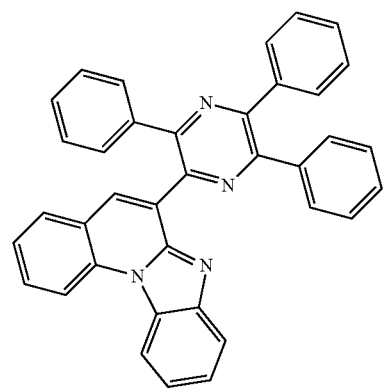
30
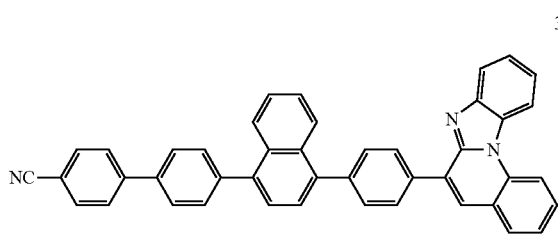
31
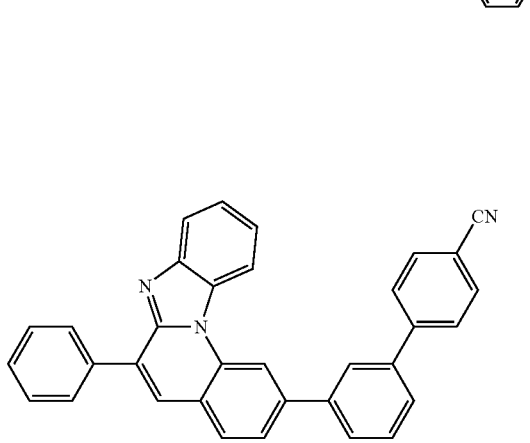

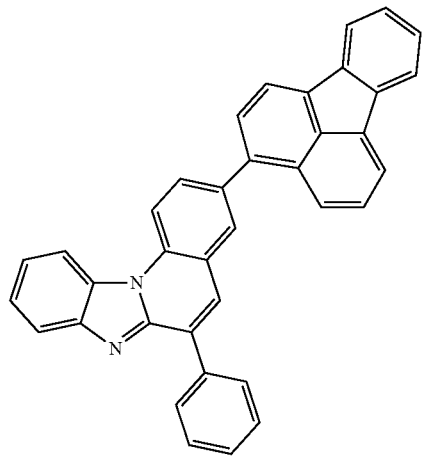
32
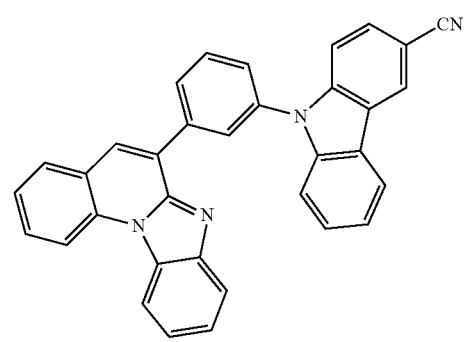
33
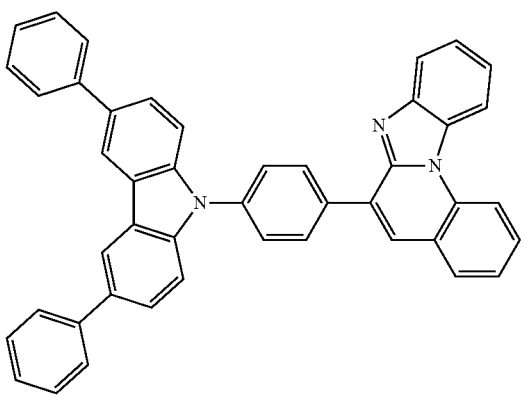
34
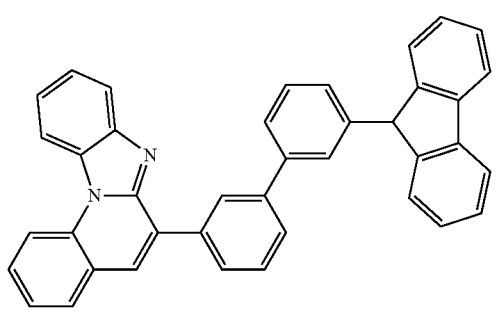
35
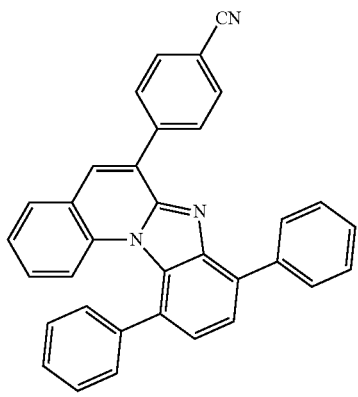
36
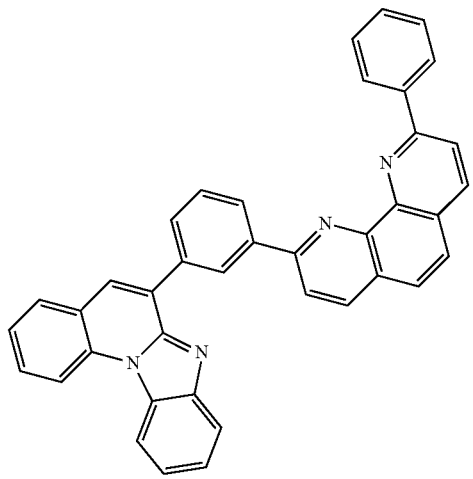
37
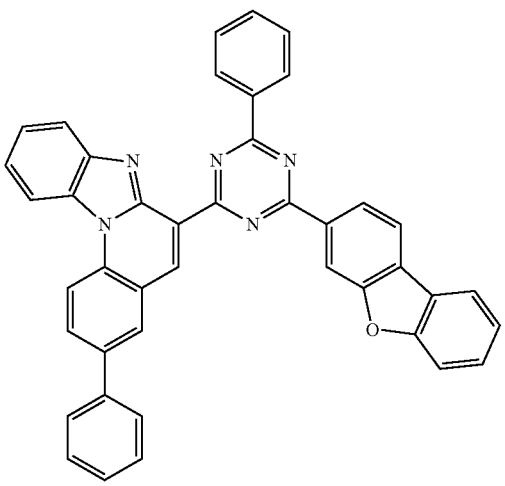
38

39
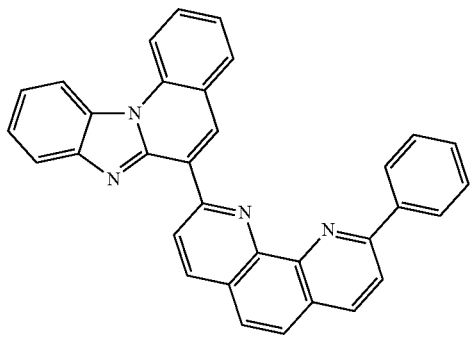
40
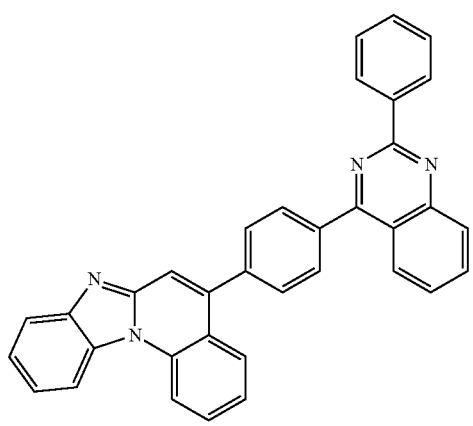
41
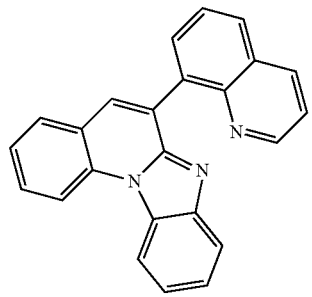
42
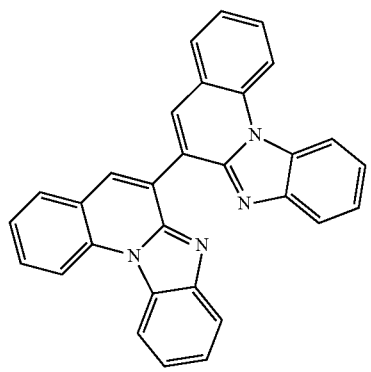
43
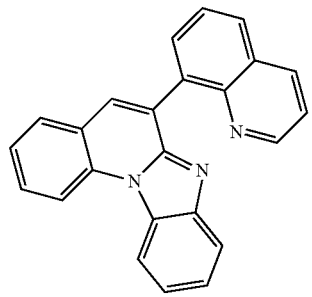
44
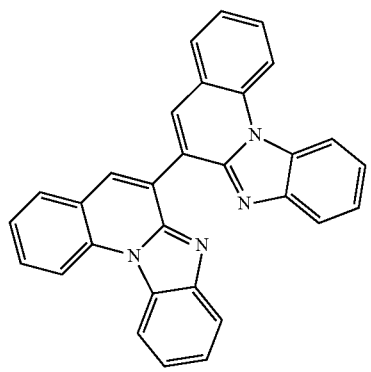
45
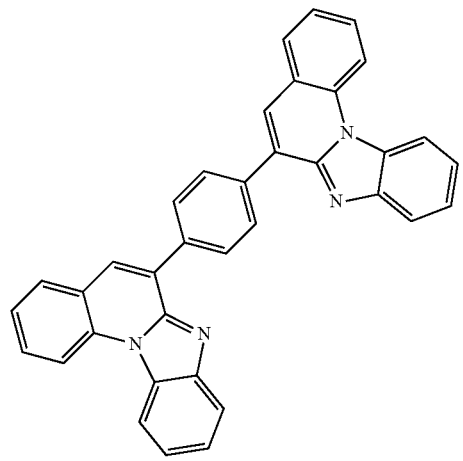
46
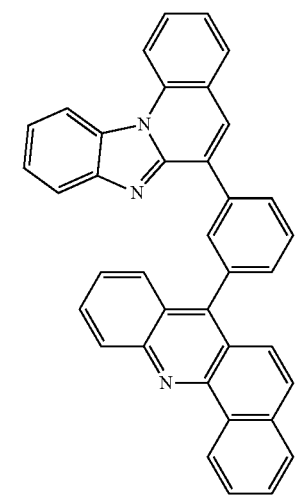

47
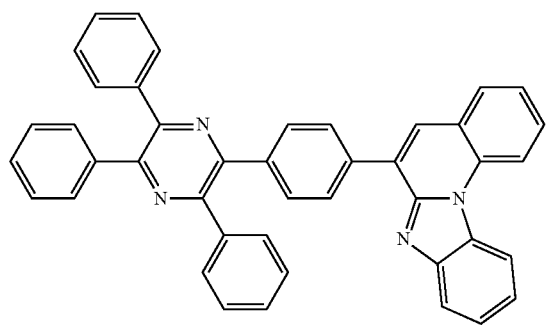
48
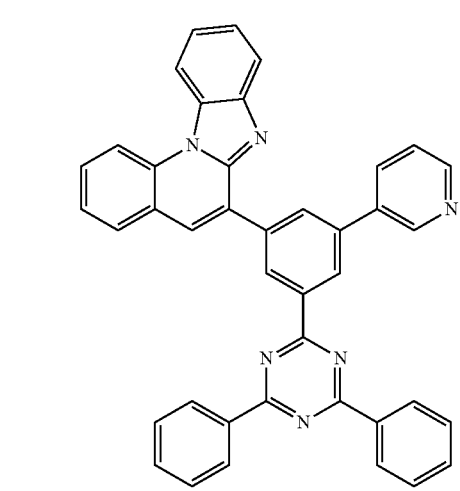
49
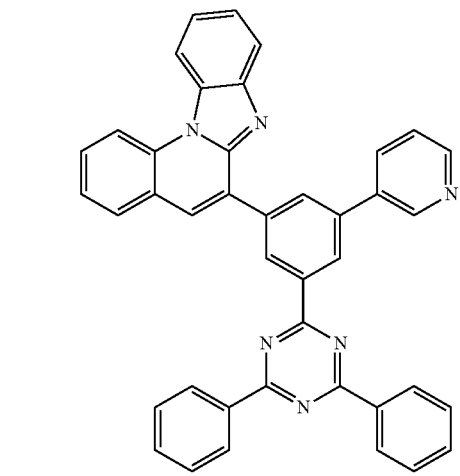
50
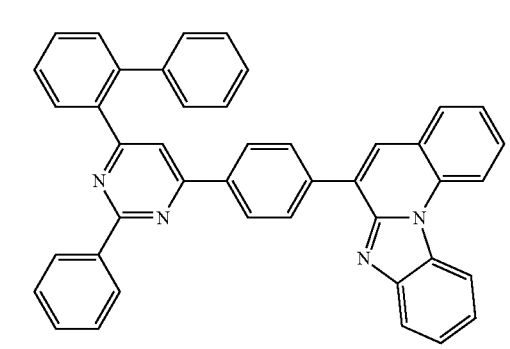
51
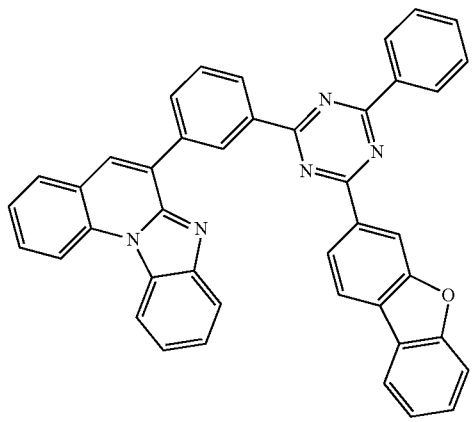
52
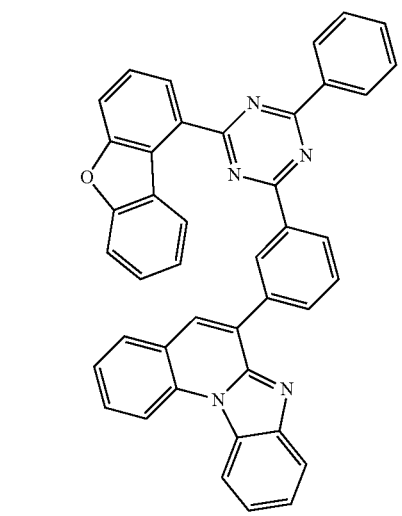
53
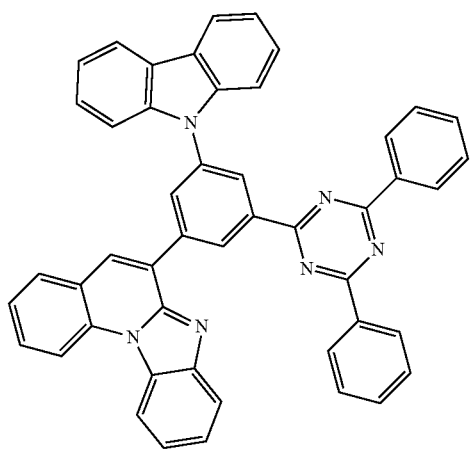

-continued

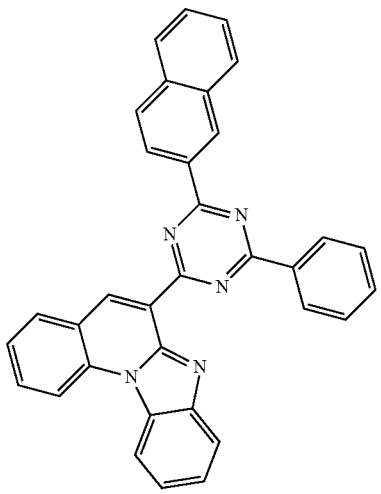

54

It may be provided that a compound represented by the following formula is excluded.

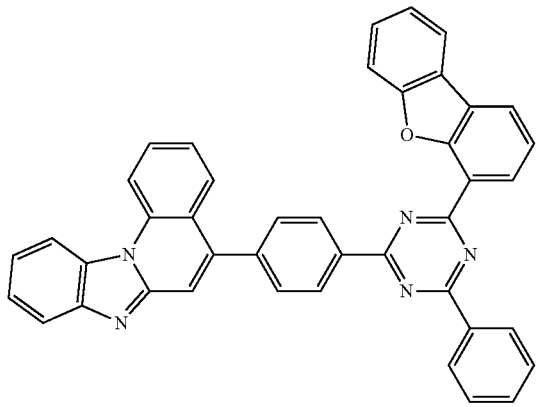 [SMILES: c1ccc(-c2nc(-c3ccc(-c4cc5nc6ccccc6n5c5ccccc45)cc3)nc(-c3cccc4c3oc3ccccc34)n2)cc1]

The object is further achieved by an organic semiconducting layer comprising the inventive compound of formula (I).

In one embodiment, the organic semiconducting layer does not contain a dopant or an additive.

In another embodiment, the organic semiconducting layer comprises an n-type additive which is selected from a metal, a metal salt and a metal complex.

The n-type additive may be an n-type dopant. The n-type dopant may be a reductive dopant in the sense that it donates an electron to the first or second matrix compound.

The organic semiconducting layer may further comprise at least one second matrix compound. The second matrix compound is not an n-type dopant or an n-ty e additive.

The metal may be selected from alkali metal, alkaline earth metal and rare earth metal.

The metal salt may be metal salt of an alkali metal, the salt of an alkaline earth metal or the salt of a rare earth metal.

The metal complex may be an organic alkali metal complex, alternatively an alkali metal complex, alternatively LiQ or alkali borate.

The organic semiconducting layer may be essentially non-emissive.

The object is further achieved by an organic electronic device comprising the inventive organic semiconducting layer.

It may be provided that the organic electronic device comprises a first electrode and a second electrode and that the organic semiconducting layer is arranged between the first electrode and the second electrode.

It may be provided that the organic electronic device comprises two emission layers and that the organic semiconducting layer is arranged between the two emission layers.

In case that the organic electronic device comprises more than two emission layers, the organic semiconducting layer may be arranged between (at least) two of them.

The organic electronic device may further comprise an auxiliary electron transport layer and the organic semiconducting layer may be arranged in direct contact with the auxiliary electron transport layer. The compound of formula (I) may be comprised in the auxiliary electron transport layer or, alternatively, the auxiliary electron transport layer may consist of the compound of formula (I).

The organic electronic device may comprise an emission layer and the semiconducting layer may be arranged in direct contact with the emission layer.

The organic electronic device may comprise an electron transport layer and the organic semiconducting layer may be arranged in direct contact with the electron transport layer.

The organic electronic device may comprise a cathode and the organic semiconducting layer may be arranged in direct contact with the cathode.

The object is further achieved by a display device comprising the inventive organic electronic device.

The object is further achieved by a lighting device comprising the inventive organic electronic device.

Embodiments and combinations thereof referred to above with respect to the inventive compound are also embodiments for realizing the organic semiconducting layer, the organic electronic device, the display device or the lighting device as described herein.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide ($SnO_2$), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MT-DATA), TDATA, 2T-NATA, polyaniline/dodecylbenzene-sulfonic acid (Pani/DBSA), poly(3,4-ethylenedioxythiophene)/poly(4-styrenesulfonate) (PEDOT/PSS), styrenesulfonate (PANI/PSS).

The HIL may comprise or consist of p-type dopant and the p-type dopant may be selected from tetrafluoro-tetracyano-quinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations can be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine(TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzothiazolate)zinc (Zn(BTZ)2).

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4,4'-bis(4-diphenyl amiostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the L comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary electron transport layer or a-ETL and electron transport layer 1 or ETL-1.

The electron transport layer 1 of the organic electronic device may comprise the compound represented by general Formula (I). Alternatively, the HBL may consist of the compound of formula (I).

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with one preferred embodiment of the invention, the electron transport layer may be the inventive organic semiconducting layer comprising the inventive compound represented by the general Formula (I) as defined herein.

In an embodiment the ETL may consist of a compound of Formula (I).

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material. The electron transport layer may comprise, besides or instead of the compound represented by the general Formula (I), further ETM materials known in the art. In one embodiment the electron transport layer comprises besides of the compound represented by the general Formula (I), one further ETM material which is referred to as a second matrix compound. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the organic semiconducting layer may comprise one or more n-type additives. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

According to another aspect of the present invention organic semiconducting layer may comprise one or more alkali metal salt and alkali metal organic complex the alkali metal salt is selected from the group comprising LiF, LiCl, LiBr or LiI, and preferably LiF;

the alkali metal organic complex is selected from the group comprising a lithium quinolinolate, lithium borate, lithium phenolate, lithium pyridinolate or comprises a lithium with a Schiff base ligand;

preferably the lithium quinolinolate complex has the formula IV, V or VI:

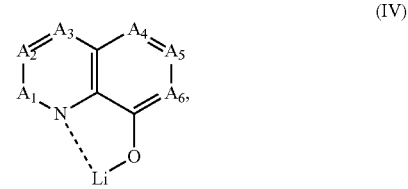

(IV)

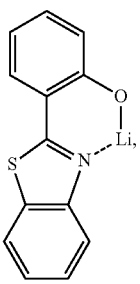
(V)

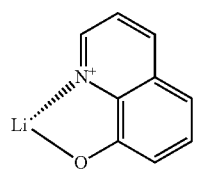
(VI)

wherein $A_1$ to $A_6$ are same or independently selected from CH, CR, N, O;

R is same or independently selected from hydrogen, halogen, alkyl or aryl or heteroaryl with 1 to 20 carbon atoms; and more preferred A1 to A6 are CH;

preferably the borate based organic ligand is a tetra(1H-pyrazol-1-yl)borate;

preferably the phenolate is a 2-(pyridin-2-yl)phenolate, a 2-(diphenylphosphoryl)phenolate, an imidazol phenolates, or 2-(pyridin-2-yl)phenolate and more preferred 2-(i-phenyl-1H-benzo[d]imidazol-2-yl)phenolate;

preferably the pyridinolate is a 2-(diphenylphosphoryl) pyridin-3-olate, preferably the lithium Schiff base has the structure 100, 101, 102 or 103:

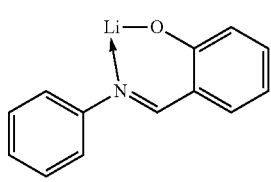
100

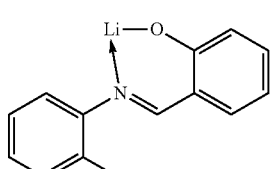
101

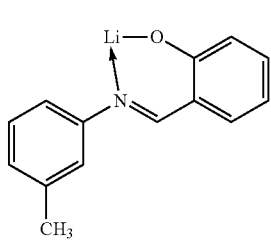
102

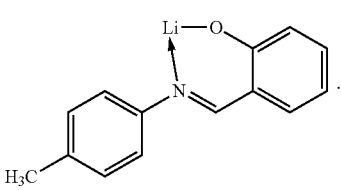
103

According to another aspect of the present invention, the OLED may comprise an electron transport layer or an electron transport layer stack comprising at least a first electron transport layer and at least a second electron transport layer wherein the first first electron transport layer may comprise the compound represented by general Formula (I).

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, Li2O, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane ($F_4$-TCNQ), derivatives of tetracyanoquinodimethane, radialene derivatives, iodine, $FeCl_3$, $FeF_3$, and $SbCl_5$. Also, the host can be one selected from a group consisting of N,N'-di(naphthalen-1-yl)-N,N-diphenylbenzidine (NPB), N,N'-diphenyl-N,N'-bis(3-methylphenyl)-1,1-biphenyl-4,4'-diamine (TPD) and N,N',N'-tetranaphthylbenzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, CS, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:
- at least one deposition source, preferably two deposition sources and more preferred at least three deposition sources.

The methods for deposition that can be suitable comprise:
- deposition via vacuum thermal evaporation;
- deposition via solution processing, preferably the processing is selected from spin-coating, printing, casting; and/or
- slot-die coating.

According to various embodiments of the present invention, there is provided a method using:
- a first deposition source to release the compound of Formula (I) according to the invention, and
- a second deposition source to release the metal, a metal salt or an alkali or alkaline earth metal complex; alternatively an organic alkali or alkaline earth metal complex; alternatively 8-hydroxyquinolinolato lithium or alkali borate;

the method comprising the steps of forming the organic semiconducting layer; whereby for an organic light-emitting diode (OLED):
- the organic semiconducting layer is formed by releasing the compound of Formula (I) according to the invention from the first deposition source and a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
- on a substrate a first anode electrode is formed,
- on the first anode electrode an emission layer is form
- on the emission layer an electron transport layer stack is formed, optionally a hole blocking layer is formed on the emission layer and an organic semiconducting layer is formed,
- and finally a cathode electrode is forme
- optional a hole injection layer, a hole transport layer, and a hole blocking layer, formed in that order between the first anode electrode and the emission layer,
- optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:

anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

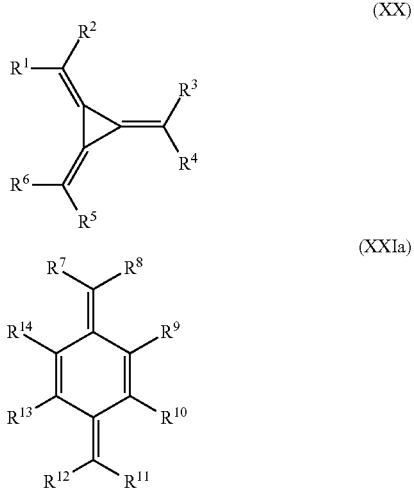

(XX)

(XXIa)

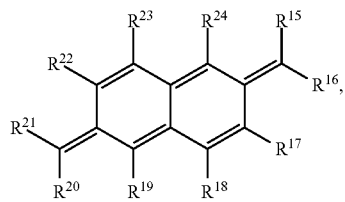

(XXIb)

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{11}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

Details and Definitions of the Invention

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass aromatic groups like phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed shall be any further aromatic hydrocarbon substituents, such as fluorenyl etc. "Arylene" respectively "heteroarylene", refers to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "condensed aryl(ene) group" refers to an aryl group comprising at least two aromatic rings which are fused to each other by sharing two carbon atoms with each other. In this regard, it may be provided that the condensed aryl group (or the condensed arylene group) comprises more than two fused rings wherein each of the rings is fused with at least one other aryl ring of the condensed aryl(ene) by sharing with this one (or more) further ring(s) two carbon atoms. Non-limiting examples of such condensed aryl groups are fluoranthenyl, chrysenyl, pyrenyl etc.

The term "alkenyl" as used herein refers to a group $—CR^1=CR^2R^3$ comprising a carbon-carbon double bond.

The term "perhalogenated" as used herein refers to a hydrocarbyl group wherein all of the hydrogen atoms of the hydrocarbyl group are replaced by halogen (F, Cl, Br, I) atoms.

The term "alkoxy" as used herein refers to a structural fragment of the Formula —OR with R being hydrocarbyl, preferably alkyl or cycloalkyl.

The term "heteroaryl" as used herein refers to aromatic or aryl groups in which at least one carbon atom is substituted with a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroaryl" as used herewith shall encompass pyridine, quinoline, benzoquinoline, quinazoline, benzoquinazoline, pyrimidine, pyrazine, triazine, benzimidazole, benzothiazole, benzo[4,5]thieno[3,2-d]pyrimidine, carbazole, xanthene, phenoxazine, benzoacridine, dibenzoacridine, dibenzofurane, dibenzothiophene, phenanthroline and the like.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound of Formula (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects d advantages of the present invention will become apparent and more readily appreciated from the following description of the exemplary embodiments, taken in conjunction with the accompanying drawings, of which.

DETAILED DESCRIPTION

Figure 1:
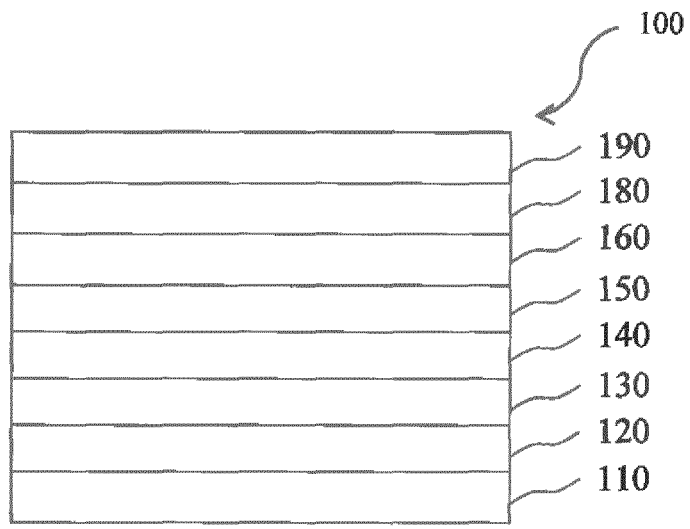
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
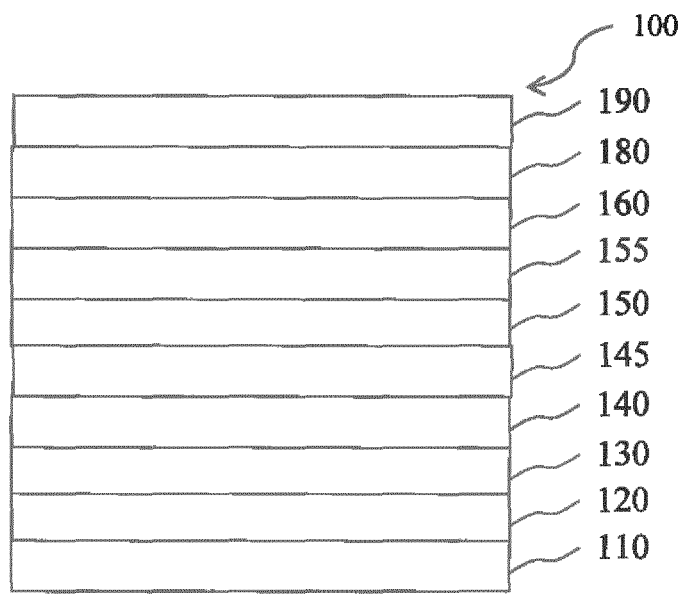
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an HBL.

Figure 3:
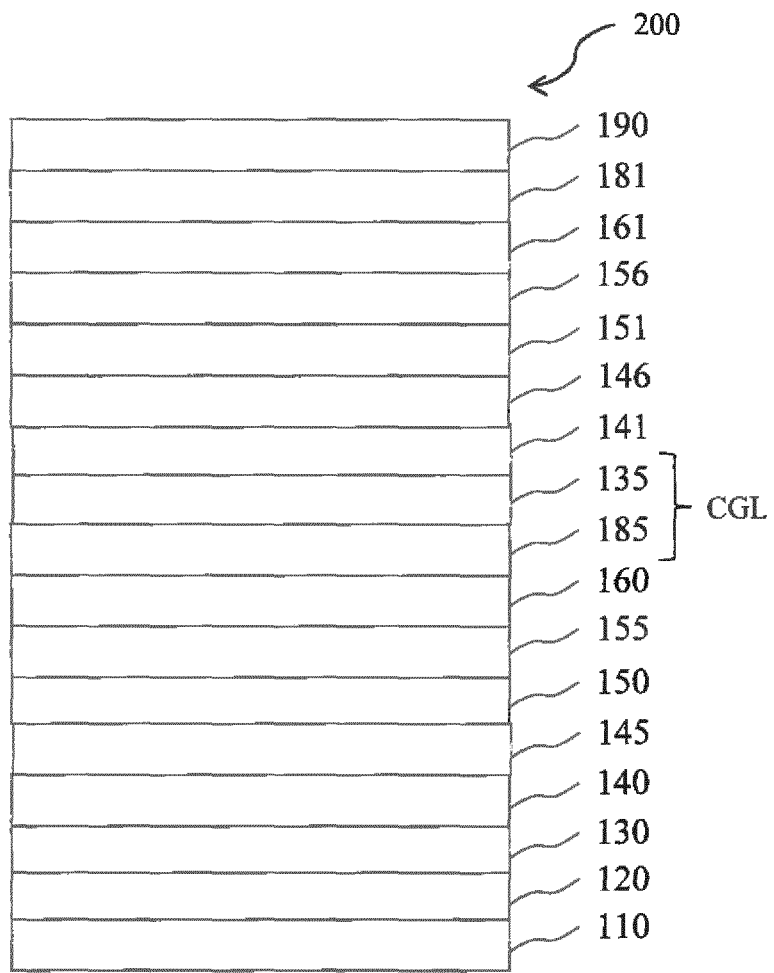
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate no, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, n-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Data

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Rate Onset Temperature

The rate onset temperature ($T_{RO}$) is determined by loading 100 mg compound into a VTE source. As VTE source a point source for organic materials may be used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard $Fc^+/Fc$ redox couple, afforded finally the values reported above. All studied compounds as well as the reported comparative compounds showed well-defined reversible electrochemical behaviour.

Dipole Moment

The dipole moment $|\vec{\mu}|$ of a molecule containing N atoms is given by:

$$\vec{\mu} = \sum_{i}^{N} q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

Calculated HOMO and LUMO

The HOMO and LUMO are calculated with the program package TURBOMOLE V6.5 (TUROMOLE GmbH, Litzenhardtstrasse 19, 76135 Karlsruhe, Germany). The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

Synthesis Procedures

General Synthetic Procedure for the Preparation of Compounds of Formula (I):

Precursor Synthesis

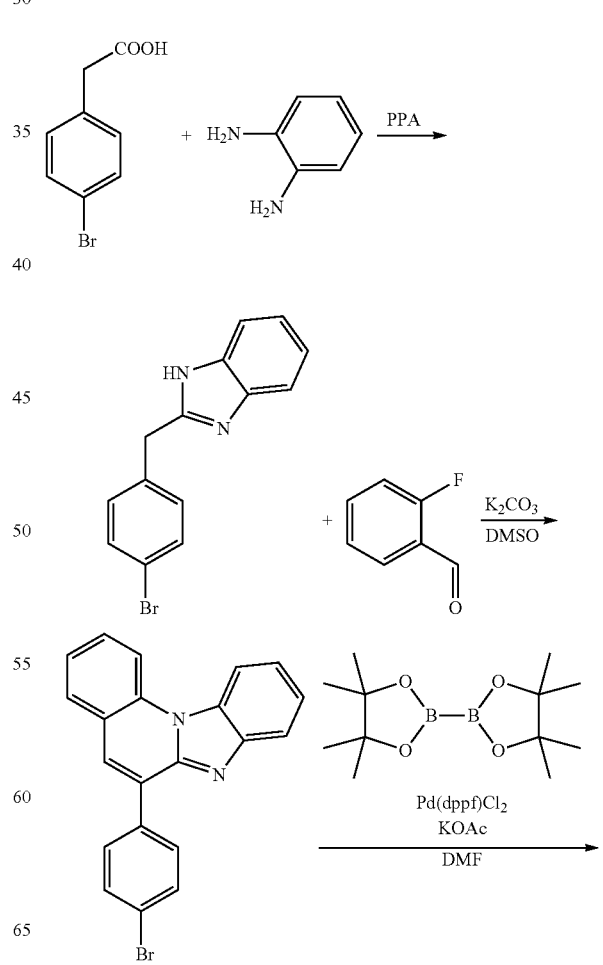

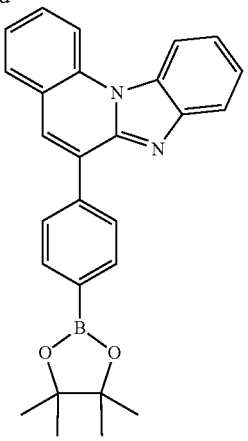

Synthesis of 2-(4-bromobenzyl)-1H-benzo[d]imidazole

In a 500 mL 4-necked flask equipped with mechanical stirrer, internal thermometer and reflux condenser, polyphosphoric acid (60 g) was heated to +50° C. internal temperature under an inert nitrogen atmosphere. Afterwards, benzene-1,2-diamine (10.56 g, 97.7 mmol, 1.05 eq) and 2-(4-bromophenyl)acetic acid (20.0 g, 93 mmol, 1.0 eq) were added and the mixture was heated to an internal temperature of +230° C. After 18 hours, the reaction was cooled down to +100° C. and added to ice/water (1,000 mL). The flask was flushed with water (150 mL) and saturated aqueous sodium bicarbonate solution (150 mL) to dissolve residues from the glass. The aqueous layers were combined and basified to pH 8 using sodium hydroxide pellets. Ethyl acetate (1,000 mL) was added and insoluble parts were removed via filtration and washed with further ethyl acetate (3×100 mL). The layers from the 2-phase filtrate were separated and the aqueous layer was re-extracted with ethyl acetate (4×250 mL). The combined extracts were washed with water (2×300 mL), dried over sodium sulphate and evaporated to dryness. The crude material (14.2 g brown solid) was dissolved in a mixture dichloromethane/1% methanol (400 mL) and filtered through a pressed pad of silica. The pad was flushed with a further 2.000 mL of the DCM/1% MeOH mixture and the combined filtrates were concentrated to a final volume of ca. 20 mL. n-Hexane (250 mL) was added and the precipitate was isolated after 15 minutes via filtration. The filter residue was washed with hexane (3×10 mL) and dried in a vacuum oven at +60° C. to give 10.0 g (37% yield) of a pale beige solid with a purity GC 99.6%/HPLC 99.8%. A 2$^{nd}$ crop was isolated from mother liquor concentration and yielded 1.5 g (5% yield) of a pale beige solid with a purity GC99.2%/HPLC 99.7%.

Synthesis of 6-(4-bromophenyl)benzo[4,5]imidazo[1,2-a]quinolone

Under an inert nitrogen atmosphere, 2-(4-bromobenzyl)-1H-benzo[d]imidazole (5.0 g, 17.4 mmol, 1.0 eq), 2-fluorobenzaldehyde (2.5 mL, 23.5 mmol, 1.35 eq) and potassium carbonate (7.21 g, 52.2 mmol, 3.0 eq) were placed in a 250 mL flask. Dimethyl sulfoxide (DMSO, 90 mL) was added in a single portion in a counterflow of nitrogen. The mixture was heated to an internal temperature of +120 C and stirred overnight, maintaining the inert conditions. After 5 hours reaction, further 2-fluorobenzaldehyde (0.4 mL, 3.5 mmol, 0.2 eq) was added to the mixture. After 23 hours the mixture was cooled down to +5° C., filtered and the filter residue was subsequently washed with DMSO (3×10 mL) and water (500 mL). The product was dried in a vacuum oven at +60° C. to give 5.2 g (80% yield) of a beige solid with a purity of GC 96.1% (+3.9% de-brominated side-product).

Synthesis of 6-(4-(4,4,5,5-tetramethyl-1,3,2-dioxaborolan-2-yl)phenyl)benzo[4,5]imidazo[1,2-a]quinolone Under an inert nitrogen atmosphere, 6-(4-bromophenyl)benzo[4,5]imidazo[1,2-a]quinolone (5.0 g, 13.4 mmol, 1.0 eq), 4,4,4',4',5,5,5',5'-octamethyl-2,2% bi(1,3,2-dioxaborolane) (3.74 g, 14.7 mmol, 1.1 eq), [1,1'-Bis(diphenyl-phosphino)ferrocene]dichloropalladium(II) (0.29 g, 0.40 mmol, 3 mol %) and potassium acetate (3.95 g, 40.2 mmol, 3.0 eq) were placed in a 250 mL flask. N,N-dimethylformamide (DMF, 60 mL) was added in a single portion in a counterflow of nitrogen. The mixture was heated to +100 C and stirred overnight, maintaining the inert conditions. After 19 hours the mixture was cooled down and the solvent was evaporated to dryness. The residue was taken into dichloromethane (DCM, 500 mL) and washed with water (3×350 mL). The organic layer was dried over magnesium sulphate and filtered through a pressed pad of Florisil®. The pad was flushed with DCM (2.5 L) and the combined filtrated were concentrated to a final volume of ca. 15 mL. n-Hexane (200 mL) was added and the precipitate was isolated after 15 minutes via filtration. The filter residue was washed with hexane (3×10 mL) and dried in a vacuum oven at +50° C. to give 4.8 g (85% yield) of a pale yellow solid with a purity GC99,81%/HPLC 99.36%.

Compound Inv-1

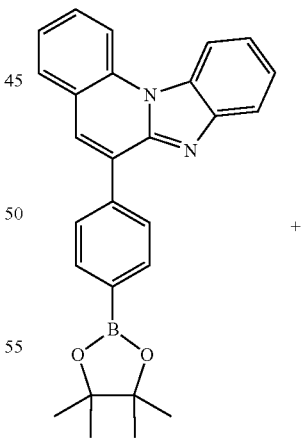

+

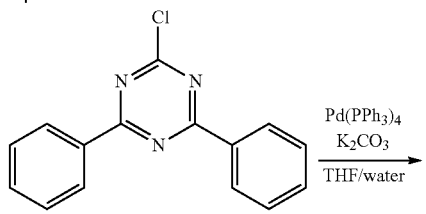

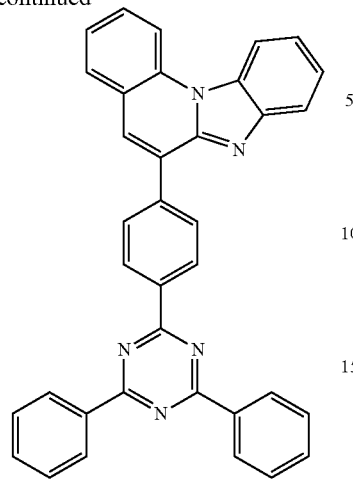

Synthesis of 6-(4-(4,6-diphenyl-1,3,5-triazin-2-yl)phenyl)benzo[4,5]imidazo[1,2-a]quinoline Under an inert nitrogen atmosphere, 6-(4-(4,4,5,5-tetramethyl-1,3,2-dioxaborolan-2-yl)phenyl)benzo[4,5]imidazo[1,2-a]quinoline (4.7 g, 11.2 mmol, 1.0 eq), 2-chloro-4,6-diphenyl-1,3,5-triazine (3.14 g, 11.7 mmol, 1.05 eq), Tetrakis(triphenylphosphin)palladium(0) (0.26 g, 0.224 mmol, 2 mol %) and potassium carbonate (3.1 g, 22.4 mmol, 2.0 eq) were placed in a 250 mL reaction vessel. Afterwards, tetrahydrofuran (THF, 28 mL) and degassed water (7 mL) were added. The pale yellow suspension was heated to +75° C. and stirred overnight, maintaining the inert atmosphere. Reaction progress was monitored using TLC (silica, chlorobenzene with 5% methanol). After 23.5 hours the mixture was cooled to room temperature, filtered and the filter residue was washed with THF (3×15 mL) and water (1.000 mL). The pale yellow solid was dissolved in hot chlorobenzene (1.500 mL), filtered (hot) through a pressed pad of silica (Ø6.5 cm, h 1 cm) and the pad was rinsed with further hot chlorobenzene (1.000 mL). A thick precipitate formed in the suction flask almost immediately. The filtrate was concentrated to a final volume of ~250 mL and stored over the weekend at room temperature. Afterwards, the precipitate was isolated via filtration, washed with chlorobenzene (3×15 mL) and dried in an oil pump vacuum at +150° C. for 2 hours. The product was obtained as 4.75 g (81% yield) of a pale yellow solid with an HPLC purity of 99.95%. Final purification was done by gradient sublimation with a sublimation yield of 87%.

Compound Inv-2

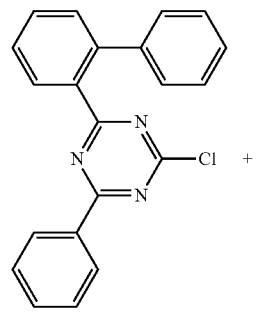 +

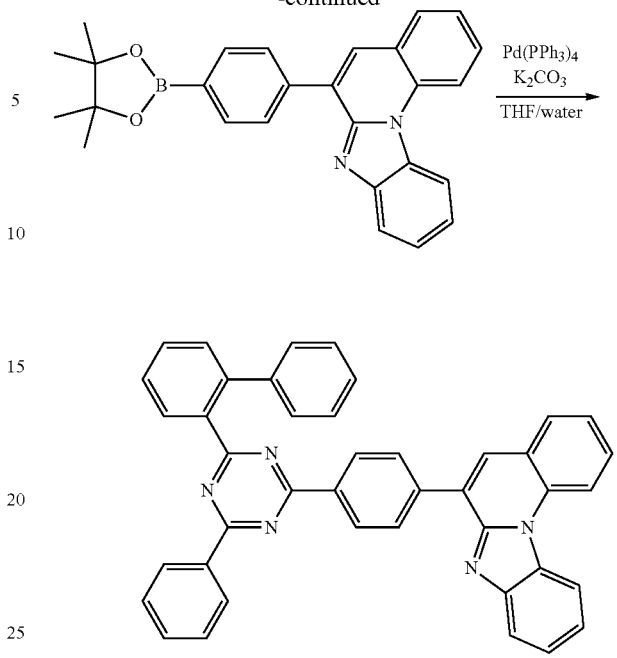

Synthesis of 6-(4-(4-([1,1'-biphenyl]-2-yl)-6-phenyl-1,3,5-triazin-2-yl)phenyl)benzo[4,5]imidazo[1,2-a]quinoline Under an inert nitrogen atmosphere, 6-(4-(4,4,5,5-tetramethyl-1,3,2-dioxaborolan-2-yl)phenyl)benzo[4,5]imidazo[1,2-a]quinoline (5.2 g, 12.4 mmol, 1.0 eq), 2-([1,1'-biphenyl]-2-yl)-4-chloro-6-phenyl-1,3,5-triazine (4.47 g, 13.0 mmol, 1.05 eq) and potassium carbonate (3.42 g, 24.7 mmol, 2.0 eq) were placed in the reaction vessel. Afterwards, tetrahydrofuran (THF, 50 mL) and degassed water (12 mL) were added. In a counterflow of nitrogen, Tetrakis(triphenylphosphin)palladium(0) (0.29 g, 0.247 mmol, 2 mol %) was added and the pale brown suspension was heated to +75° C. and stirred overnight, maintaining the inert atmosphere. Reaction progress was monitored using TLC (silica, dichloromethane with 5% methanol). After complete conversion, the mixture was cooled to room temperature, concentrated to a minimum volume and water and chloroform were added. The layers were separated and the organic layer was washed with water, dried over sodium sulphate and evaporated to dryness. Undissolved solid parts from the 2-phase system were filtered prior to layer separation and combined with the crude material. Afterwards, the crude material was dissolved in hot tetrahydrofuran (THF, 250 mL) and filtered (hot) through a pressed pad of silica (Ø5 cm, h 0.7 cm) and the pad was rinsed with further hot THF (200 mL). The filtrate was concentrated to a final volume of ca. 20 mL, cooled to room temperature and n-hexane (80 mL) was added. The suspension was stirred overnight, filtered and the filter residue was washed with n-hexane and dried in vacuo at +50° C. overnight. Re-precipitation from chloroform (98 mL)/n-hexane (100 mL) followed by re-crystallization from chlorobenzene (60 mL) and drying under vacuum at +120° C. gave 5.2 g (70% yield) of a pale yellow solid with an HPLC purity of 100%. Final purification was done by gradient sublimation with a sublimation yield of 81%.

41

Synthesis of 5-phenyl-6-(4-(4,4,5,5-tetramethyl-1,3,2-dioxaborolan-2-yl)phenyl)benzo[4,5]imidazo[1,2-a]quinoline

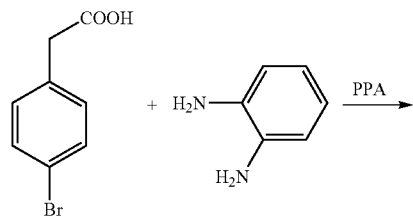

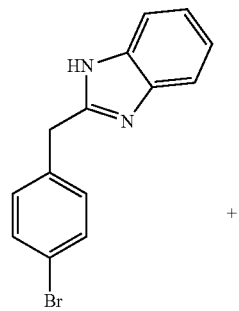

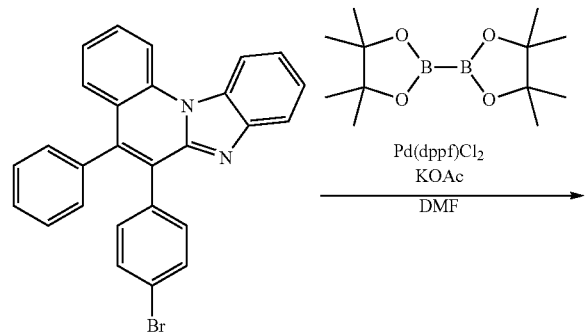

-continued

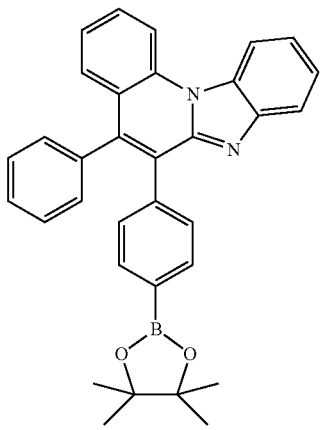

Following the above described procedures, 6-(4-bromophenyl)-5-phenylbenzo[4,5]imidazo[1,2-a]quinolone and 5-phenyl-6-(4-(4,4,5,5-tetramethyl-1,3,2-dioxaborolan-2-yl)phenyl)benzo[4,5]imidazo[1,2-a]quinolone were obtained as outlined in the scheme above in 78% and 93% yield, respectively, and with an HPLC purity of 99.7% and 99.2%, respectively.

Compound Inv-3

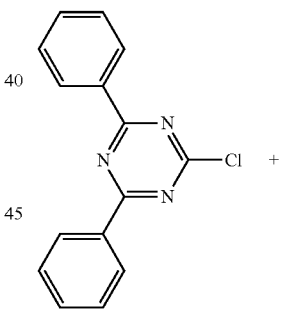

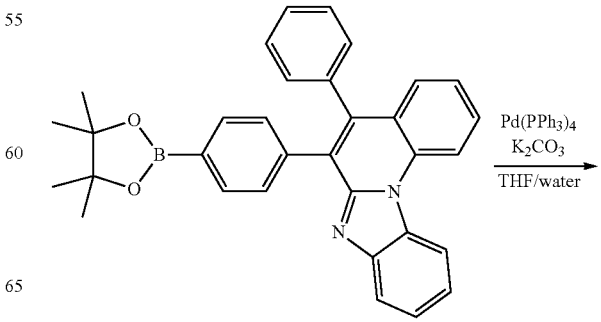

-continued

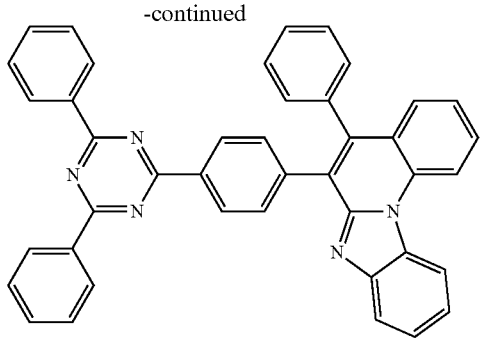

Synthesis of 6-(4-(4,6-diphenyl-1,3,5-triazin-2-yl)phenyl)-5-phenylbenzo[4,5]imidazo[1,2-a]quinoline Under an inert nitrogen atmosphere, 5-phenyl-6-(4-(4,4,5,5-tetramethyl-1,3,2-dioxaborolan-2-yl)phenyl)benzo[4,5]imidazo[1,2-a]quinoline (15 g, 30 mmol, 1.0 eq), 2-chloro-4,6-diphenyl-1,3,5-triazine (8.49 g, 32 mmol, 1.05 eq) and potassium carbonate (8.35 g, 60 mmol, 2.0 eq) were placed in the reaction vessel. Afterwards, tetrahydrofuran (THF, 120 mL) and degassed water (30 mL) were added. In a counterflow of nitrogen, Tetrakis(triphenylphosphin)palladium(0) (0.69 g, 0.06 mmol, 2 mol %) was added and the thin suspension was heated to +75° C. and stirred for 65 h, maintaining the inert atmosphere. Reaction progress was monitored using TLC (silica, dichloromethane). After complete conversion, the mixture was cooled to room temperature and the solid filtered off. The filter cake is rinsed with water (until pH test reacts neutral) and methanol. Then the solid is dissolved in 500 mL hot DCM and filtered through a pressed pad of silica (Ø8 cm, h 3 cm). The filtrate was concentrated to a final volume of ca. 60 mL, cooled to room temperature and n hexane was added. The suspension was stirred, filtered and the filter residue was washed with n hexane and dried in vacuo at 50° C. overnight. Re-crystallization from DMF (500 mL) and drying under vacuum at +120° C. gave 11.3 g (62% yield) of an off-white solid with an HPLC purity of 99.93%. Final purification was done by gradient sublimation with a sublimation yield of 77%.

General Procedure for Fabrication of OLEDs

For the top emission OLED devices of example-1 and of the comparative example a substrate with dimensions of 150 mm×150 mm×0.7 mm was ultrasonically cleaned with a 2% aquatic solution of Deconex FPD 211 for 7 minutes and then with pure water for 5 minutes, and dried for 15 minutes in a spin rinse dryer. Subsequently, Ag was deposited as anode at a pressure of 10-5 to 10-7 mbar.

Then, HT-1 and D-1 were vacuum co-deposited on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1.

Then, the ET-1 was vacuum deposited onto the emission layer to form the hole blocking layer (HBL). Then, the electron transport layer was formed on the hole blocking layer by co-depositing a compound of formula (I) and LiQ.

Then, the electron injection layer is formed on the electron transporting layer by deposing Yb.

Ag:Mg is then evaporated at a rate of 0.01 to 1 Å/s at 10-7 mbar to form a cathode.

A cap layer of HT-1 is formed on the cathode.

The details of the layer stack in the top emission OLED devices are given below. A slash "/" separates individual layers. Layer thicknesses are given in squared brackets [ . . . ], mixing ratios in wt % given in round brackets ( . . . ):

Layer Stack Details:

Ag [100 nm]/(92:8) [10 nm]/HT-1 [118 nm]/HT-2 [5 nm]/H09:BD200 (97:3) [20 nm]/ET-1 [5 nm]/Compound of formula (I):LiQ (1:1) [31 nm]/Yb [2 nm]/Ag:Mg (9:1) [13 nm]/HT-1 [70 nm]

Technical Effect of the Invention

The OLED devices according to the invention show improved EQE efficiency, lifetime and lower operating voltage when using the compounds of formula (I) in an electron transport layer instead of the prior art compound.

LIST OF COMPOUNDS USED

| | IUPAC name | Reference |
|---|---|---|
| HT-1 | N-([1,1'-biphenyl]-4-yl)-9,9-dimethyl-N-(4-(9-phenyl-9H-carbazol-3-yl)phenyl)-9H-fluoren-2-amine [CAS 1242056-42-3] | US2016322581 |
| HT-2 | N,N-bis(4-(dibenzo[b,d]furan-4-yl)phenyl)-[1,1':4',1''-terphenyl]-4-amine [CAS 1198399-61-9] | JP2014096418 |
| D-1 | 4,4',4''-((1E,1'E,1''E)-cyclopropane-1,2,3-triylidenetris(cyanomethanylylidene))tris(2,3,5,6-tetrafluorobenzonitrile) [CAS 1224447-88-4] | US2008265216 |
| HOST-1 | H09 (Fluorescent-blue host material) | Commercially available from Sun Fine Chemicals, Inc, S. Korea |
| EMITTER-1 | BD200 (Fluorescent-blue emitter material) | Commercially available from Sun Fine Chemicals, Inc, S. Korea |
| ET-1 | 2,4-diphenyl-6-(4',5',6'-triphenyl-[1,1':2',1'':3'',1''':3''',1''''-quinquephenyl]-3''''-yl)-1,3,5-triazine [CAS 2032364-64-8] | WO2016171358 |
| Comparative-1 | 4,4'-bis(4,6-diphenyl-1,3,5-triazin-2-yl)biphenyl [CAS 266349-83-1] | Organic Electronics, 2008, 9(3), p285 |
| LiQ | 8-Hydroxyquinolinolato-lithium [CAS 850918-68-2] | WO2013079217 |

TABLE 1

Properties of compounds Inv-1 to Inv-3 and of compound Comparative-1

| | Molecular Structure | Dipole moment [Debye] | mp [0° C.] | Tg [0° C.] | $T_{RO}$ [0° C.] |
|---|---|---|---|---|---|
| Comparative-1 | 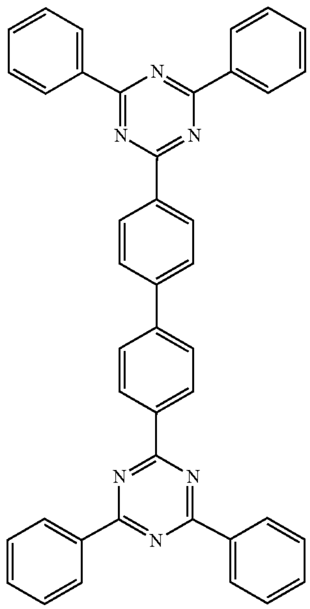 [SMILES: c1ccc(-c2nc(-c3ccccc3)nc(-c3ccc(-c4ccc(-c5nc(-c6ccccc6)nc(-c6ccccc6)n5)cc4)cc3)n2)cc1] | 0.02 | 366 | — | 262 |
| Inv-1 | 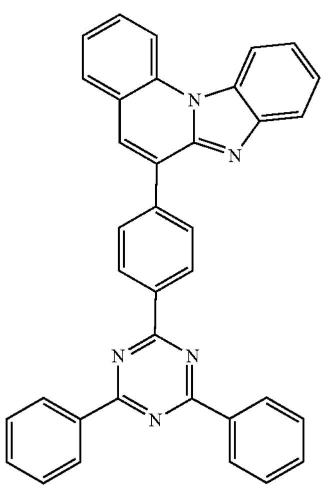 [SMILES: c1ccc(-c2nc(-c3ccccc3)nc(-c3ccc(-c4cc5ccccc5n5c4nc4ccccc45)cc3)n2)cc1] | 3.10 | 361 | 124 | 262 |
| Inv-2 | 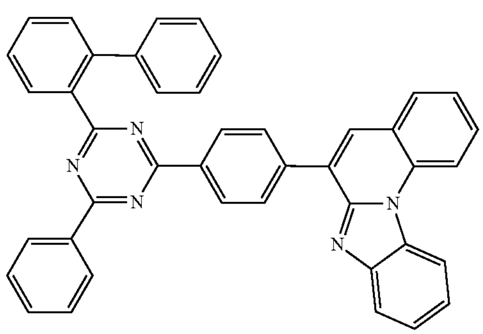 [SMILES: c1ccc(-c2nc(-c3ccc(-c4cc5ccccc5n5c4nc4ccccc45)cc3)nc(-c3ccccc3-c3ccccc3)n2)cc1] | 3.08 | 251 | 118 | 245 |

TABLE 1-continued

Properties of compounds Inv-1 to Inv-3 and of compound Comparative-1

| | Molecular Structure | Dipole moment [Debye] | mp [0° C.] | Tg [0° C.] | $T_{RO}$ [0° C.] |
|---|---|---|---|---|---|
| Inv-3 | 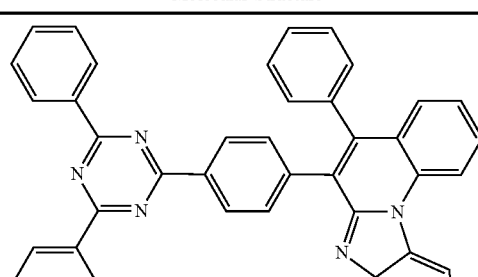 | 3.36 | 349 | 162 | 272 |

Dipole moment simulated by DFT (B3LYP_Gaussian/6-31 G*, gas phase)

TABLE 2

Performance of a top emission OLED comprising the compounds of formula (1) and the compound comparative-1 in the electron transport layer.

| OLED device examples | Matrix material | n-additive | Operating voltage at 10 mA/cm² (V) | EQE at 10 mA/cm² | Lifetime LT97 at 30 mA/cm² [h] |
|---|---|---|---|---|---|
| Comparative example | Comparative-1 | LiQ | 3.71 | 5.91 | 66 |
| Example-1 | Inv-1 | LiQ | 3.64 | 7.00 | 100 |
| Example-2 | Inv-2 | LiQ | 3.58 | 7.02 | 77 |

The features disclosed in the foregoing description and in the dependent claims may, both separately and in any combination thereof, be material for realizing the aspects of the disclosure made in the independent claims, in diverse forms thereof.

The invention claimed is:

1. Compound having the formula (I)

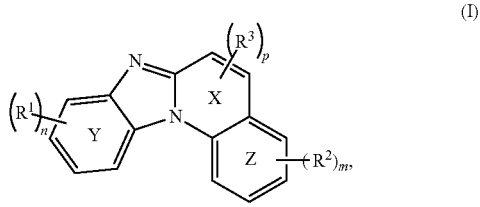

(I)

wherein n and m are independently selected integers from 0 to 2, wherein in case that n=2 the $R^1$ can be the same or different from each other, and in case that m=2 the $R^2$ can be the same or different from each other;

p is 1 or 2, wherein in case that p=2 the $R^3$ can be the same or different from each other;

$R^1$ and $R^2$ are independently selected from the group consisting of substituted or unsubstituted $C_6$ to $C_{48}$ aryl and substituted or unsubstituted $C_2$ to $C_{42}$ heteroaryl, wherein the one or more substituent(s), if present, are selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, P(=O)$R_2$, wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{20}$ cyclic thioalkyl, $C_6$ to $C_{20}$ aryl and $C_2$ to $C_{20}$ heteroaryl;

each $R^1$ and $R^2$ may be linked to the respective ring Y or Z by a first spacer unit which is independently selected from substituted or unsubstituted $C_6$ to $C_{18}$ arylene or substituted or unsubstituted $C_2$ to $C_{20}$ heteroarylene, wherein the one or more substituent(s), if present, are independently selected from the group consisting of deuterium, CN, P(=O)R'R", $C_6$ to $C_{14}$ aryl or $C_2$ to $C_{20}$ heteroaryl, wherein R' and R" may be the same or different and are independently selected from $C_1$ to $C_{10}$ alkyl or $C_6$ to $C_{12}$ aryl;

$R^3$ is independently selected from substituted or unsubstituted $C_6$ to $C_{60}$ aryl or substituted or unsubstituted $C_2$ to $C_{60}$ heteroaryl, wherein the one or more substituent(s), if present, are independently selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, P(=O)$R_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

each $R^3$ may be linked to the ring X by a second spacer unit independently selected from substituted or unsubstituted $C_6$ to $C_{18}$ aryl or substituted or unsubstituted $C_2$ to $C_{20}$ heteroaryl, wherein the one or more substituent (s), if present, are independently selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, P(=O)$R_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

positions of the rings X, Y and Z which are not directly linked to either $R^1$, $R^2$, $R^3$, the first spacer unit, the second spacer unit or hydrogen may be bound to a substituent selected from the group consisting of deuterium, fluorine, RF, $C_1$ to $C_{20}$ linear alkyl, $C_3$ to $C_{20}$ branched alkyl, $C_1$ to $C_{12}$ linear fluorinated alkyl, CN, RCN, $C_6$ to $C_{20}$ aryl, $C_2$ to $C_{20}$ heteroaryl, P(=O)$R_2$, wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{30}$ cyclic thioalkyl, $C_6$ to $C_{20}$ aryl and $C_2$ to $C_{20}$ heteroaryl;

provided that if p=1, n=0 and m=0 then it is excluded that $R^3$ is 1H-benzo[d]imidazolyl connected to the ring X without the second spacer unit.

2. Compound according to claim 1, wherein the total number of aromatic rings in the Formula (I) is from 5 to 15.

3. Compound according to claim 1, wherein the first spacer unit is selected from the group consisting of substituted or unsubstituted $C_6$ to $C_{18}$ arylene or substituted or unsubstituted N-containing $C_3$ to $C_5$ heteroarylene.

4. Compound according to claim 1, wherein the groups $R^1$ and $R^2$ are independently selected from substituted or unsubstituted $C_6$ to $C_{18}$ aryl, substituted or unsubstituted N-containing $C_3$ to $C_5$ heteroaryl or substituted or unsubstituted O-containing $C_4$ to $C_{12}$ heteroaryl.

5. Compound according to claim 1, wherein n=0 and/or m=0.

6. Compound according to claim 1, wherein the second spacer unit is independently selected from the group consisting of substituted or unsubstituted $C_6$ to $C_{14}$ arylene and substituted or unsubstituted N-containing $C_3$ to $C_{12}$ heteroarylene.

7. Compound according to claim 1, wherein $R^3$ is independently selected from the group consisting of substituted or unsubstituted $C_6$ to $C_{18}$ aryl, substituted or unsubstituted O-containing $C_6$ to $C_{12}$ heteroaryl and substituted or unsubstituted N-containing $C_3$ to $C_{15}$ heteroaryl.

8. Compound according to claim 1, wherein the one or more substituent(s), if present in one or more of $R^1$, $R^2$, $R^3$, the first spacer unit and the second spacer unit, are independently selected from $C_6$ to $C_{14}$ aryl, N-containing $C_5$ to $C_{12}$ heteroaryl, O-containing $C_5$ to $C_{12}$ heteroaryl, CN, CN-substituted phenyl, P(=O)(CH$_3$)$_2$-substituted phenyl, P(=O)$R_2$ with $R_2$ being $C_1$ to $C_6$ alkyl or $C_6$ aryl.

9. Organic semiconducting layer comprising the compound of Formula (I) according to claim 1.

10. Organic semiconducting layer according to claim 9, wherein the organic semiconducting layer does not contain a dopant or an additive.

11. Organic semiconducting layer according to claim 9, wherein the organic semiconducting layer comprises an n-type additive wherein the n-type additive is selected from a metal, a metal salt or a metal complex.

12. Organic semiconducting layer according to claim 9, wherein the organic semiconducting layer further comprises at least one second matrix compound.

13. Organic electronic device comprising the organic semiconducting layer according to claim 9.

14. Display device comprising the organic electronic device according to claim 13.

15. Lighting device comprising the organic electronic device according to claim 13.

* * * * *